(12) United States Patent
Corey et al.

(10) Patent No.: US 7,838,296 B2
(45) Date of Patent: Nov. 23, 2010

(54) METHODS AND APPARATUS FOR ULTRASONIC DETERMINATION OF RED BLOOD CELL INDICES

(75) Inventors: Scott Corey, Hydes, MD (US); John Sakers, Baltimore, MD (US); Keith Lipford, Severna Park, MD (US); Samuel Reed, North Garden, VA (US); Brian Murphy, Erial, NJ (US)

(73) Assignee: Separation Technology, Inc., Sanford, FL (US)

( * ) Notice: Subject to any disclaimer, the term of this patent is extended or adjusted under 35 U.S.C. 154(b) by 1741 days.

(21) Appl. No.: 10/229,030

(22) Filed: Aug. 28, 2002

(65) Prior Publication Data

US 2004/0054283 A1    Mar. 18, 2004

(51) Int. Cl.
*G01N 31/00* (2006.01)

(52) U.S. Cl. .............................. 436/10; 436/63; 436/66; 436/70

(58) Field of Classification Search ......... 600/437–455; 424/9.5, 9.51, 9.52, 450, 489, 9.71; 436/10, 436/63, 66, 70
See application file for complete search history.

(56) References Cited

U.S. PATENT DOCUMENTS

| | | | | |
|---|---|---|---|---|
| 4,854,170 A | * | 8/1989 | Brimhall et al. | 73/570 |
| 4,993,418 A | * | 2/1991 | Weaver et al. | 600/454 |
| 5,125,264 A | * | 6/1992 | Beuzard et al. | 73/61.75 |
| 5,139,328 A | * | 8/1992 | Baker et al. | 356/39 |
| 5,833,602 A | * | 11/1998 | Osemwota | 600/310 |
| 5,928,180 A | * | 7/1999 | Krivitski et al. | 604/6.09 |
| 5,952,560 A | * | 9/1999 | Collings et al. | 73/61.75 |
| 6,029,507 A | * | 2/2000 | Faber et al. | 73/61.75 |
| 6,461,570 B2 | * | 10/2002 | Ishihara et al. | 422/65 |
| 6,521,211 B1 | * | 2/2003 | Unger et al. | 424/9.52 |
| 6,542,761 B1 | * | 4/2003 | Jahn et al. | 600/310 |
| 6,592,818 B2 | * | 7/2003 | Ishihara et al. | 422/62 |

OTHER PUBLICATIONS

Shung, Koping Kirk, On the ultrasound scattering from blood as a function of hematocrit, IEEE Transactions on Sonics and Ultraconics, vol. SU-29, No. 6, Nov. 1982.
Shung, K.K. et al., Accoustic measurement of erythrocyte compressibility, J.Acoust.Soc. Am. 72(5), Nov. 1982.

* cited by examiner

*Primary Examiner*—Long V Le
*Assistant Examiner*—Sanjay Cattungal
(74) *Attorney, Agent, or Firm*—Ober, Kaler, Grimes & Shriver; Royal W. Craig

(57) ABSTRACT

The present invention provides an apparatus and method for measuring the properties of blood using ultrasound. The present invention is particularly suitable for measuring HCT, HGB, MCV, RBC, MCHC, MCH or TPC of blood.

41 Claims, 8 Drawing Sheets

METHODS AND APPARATUS FOR ULTRASONIC DETERMINATION OF RED BLOOD CELL INDICES

STATEMENT OF GOVERNMENT

This invention was made with government support under gram number 111.63587-03 awarded by the National Hear, Lung, and Blood Institute at the National Institute of Health. The Government has certain rights in the invention.

BACKGROUND OF THE INVENTION

1. Field of the Invention

The present invention relates to a method and apparatus for measuring one or more of the hematocrit, hemoglobin concentration, mean corpuscular volume, red blood cell count, mean cellular hemoglobin, mean cellular hemoglobin concentration, and total protein concentration of a blood sample.

2. Discussion of the Background

Physicians routinely test blood parameters as part of the diagnostic process. The complete blood count (CBC) is the most common of these tests. Physicians use the results to assess the quantity and the condition of the blood's cellular components. Three of the elements of the complete blood count are used to describe the size and number of red blood cells in the sample: the hematocrit, the mean corpuscular volume, and the red blood cell count. Furthermore, four more blood properties describe the oxygen-carrying capacity of the red blood cells: the hemoglobin concentration, total protein concentration, the mean cellular hemoglobin, and the mean cellular hemoglobin concentration.

HCT—Hematocrit—(typical units: percent or unitless ratio)

HGB—Hemoglobin Concentration (typical units: g/dl)

MCV—Mean Cellular Volume (typical units: fl)

RBC—Red Blood Cell Count (typical units: cells per $\mu$l)

MCHC—Mean Cellular Hemoglobin Concentration (typical units: g/dl)

MCH—Mean Cellular Hemoglobin (typical units: pg)

TPC—Total Protein Concentration (typical units: g/dl)

Hematocrit (HCT) is one of the most important blood parameters to be calculated by the CBC. HCT is defined as the portion of the total volume of blood occupied by red blood cells. This volume fraction may be expressed as a decimal (e.g., liter/liter) or as a percentage (e.g., liter/liter×100%). HCT measurements typically provide the same information to the physician as the hemoglobin concentration (HGB) or total protein concentration (TPC)—the oxygen carrying capacity of the blood—because under normal physiological conditions almost all of the total protein in the blood is hemoglobin and it is contained in the red blood cells.

Mean Corpuscular Volume (MCV) is the average of the red blood cell volume. The Red Blood Cell Count (RBC) is an expression of the number of red blood cells per unit volume of blood, typically, cells per microliter ($\mu$l). Mean Cellular Hemoglobin (MCH) is the average mass of hemoglobin that can be found in each red blood cell. In contrast, Mean Cellular Hemoglobin Concentration (MCHC) is the average concentration (instead of mass) of hemoglobin in red blood cells.

These blood properties, in particular HCT or HGB, can be used to diagnose anemia, acute blood loss, dehydration, and scores of other conditions. HCT or HGB can also be used to assess the oxygen carrying capability of the blood. Physicians monitor HCT and HGB both acutely and chronically and may act on changes of as little as two percent (2%) of the measured value.

These seven blood metrics are intrinsically related and dependent. For example, one relation between the above properties is that the concentration of hemoglobin in a blood cell is simply the mass of hemoglobin divided by the volume it occupies: MCHC=MCH/MCV meaning MCHC can be calculated from the other two instead of being independently measured. Among the other components of blood that are characterized in a complete blood count include white blood cells and platelets. Whole blood is defined as blood that includes red blood cells, white blood cells, platelets, and all the normal components of blood.

In the hospital environment, the blood lab routinely performs complete blood counts. Blood samples are drawn into vials and delivered to the central blood lab where an automated system performs the testing. The results are relatively accurate, but not immediately available (typically requires 10 minutes to 1 hour). Alternatively, some handheld blood parameter devices provide measurements of HCT or HGB at the point of care, but the relative inaccuracy inherent in these devices limits their diagnostic value to that of a screening test.

In the emergency medical environment, there is currently no method to measure HCT in the field. The handheld devices described above are difficult to use or are not sufficiently accurate. Patients requiring a hematocrit measurement, such as victims of trauma or disaster, must await transport to a hospital or clinic with a blood lab before this information is available. If this information were available in the field, it would improve the ability of medical personnel to triage patients and speed the delivery of appropriate medical care when the patient arrived at the hospital.

In the field, it can be difficult to assess the extent to which an injured patient has bled internally. A patient's HCT decreases with blood loss. Consequently, successive HCT measurements provide a valuable indication of the degree of blood loss. In cases where the emergency medical personnel are overwhelmed by the number of injured, a device which quickly measures the HCT of those in need of medical care would greatly improve the ability of the emergency medical personnel to focus their attention on critical cases. Thus, the public emergency medical industry and the military have a significant need for a device and method capable of measuring HCT quickly, accurately and at point-of-care.

Private practice physicians who need accurate measurements of HCT are currently limited to sending blood samples to a contract blood lab, or performing slow, imprecise manual techniques that are subject to human error such as spun hematocrit or microscopic inspection.

Four methods are currently available to measure HCT:

centrifuge, cell count, optical characteristics, and electrical characteristics.

The centrifuge method is the most basic measurement technique. These centrifuges are not portable. To measure HCT, a blood sample is drawn and spun in a centrifuge (e.g. READACRIT®) for a fixed duration (typically five to thirty minutes, depending on protocol). The spin separates the blood sample into three layers. The top layer is the plasmas made up primarily of water and dissolved solids. The next layer is the thin buffy coat, made up of white blood cells, plasma proteins, and platelets. The bottom layer contains closely packed red blood cells. A technician reads the volume fraction directly using a scale. Spun hematocrit accuracy can be affected by user error in reading the scale, plasma entrapped in the red blood cell column, and distortion of red blood cell size. Typically, the resulting accuracy of a spun hematocrit performed to protocol is 2 to 5% of the measured value. The accuracies in this document are reported as the 95% confidence intervals around the mean.

Cell counting is the most direct of the measurement techniques. The blood sample is diluted to a known ratio and individual cells are counted either manually or automatically. Manual cell counting techniques are tedious and proper preparation of the sample depends on the skill of the operator. Automated cell counters (e.g. COULTER@ GEN S™ System) typically offer 1-minute sample turnaround, claim accuracies to 2.0-3.5% of the measured value, and reduce tedium and operator dependence. As a practical matter, the turnaround time at the point of care is typically 30 minutes to 12 hours, because blood samples must be transported from the patient to the centrally located lab, processed, and the results must be reported back to the point of care. Furthermore, automated systems are typically expensive and are not portable.

The optical measurement technique is relatively new. Devices employing this technique measure the amount of light transmitted through, or reflected from, flowing blood. These devices (e.g. 3M™ CDI™ System 500) are designed for use during cardiac surgery, require a blood circuit, and are not portable.

HemoCue®, is an example of a handheld device that photometrically measures the blood hemoglobin concentration. Such portable photometric devices have a 1-minute cycle time, but the accuracy is typically around 3%. A portable device with greater accuracy would be valuable because physicians make decisions based on changes as small as 1-2% of the reading.

Electrical conductivity is currently used to measure a variety of blood parameters, including hematocrit. The i-STAT® system, for example, measures the conductivity of a blood sample, corrects for ion concentrations, assumes normal white blood cell and protein levels and then calculates and reports hematocrit. While instruments that use electrical conductivity are portable, the accuracy of a typical conductivity-based hematocrit reading is ±6%, which substantially reduces the clinical value.

In the field of blood ultrasonics, much investigation has focused on analyzing ultrasonic backscatter in devices that measure blood flow velocity using the Doppler effect. These studies are useful for understanding the interaction between ultrasound and blood. Also, many researchers have explored the ultrasonic characteristics of blood for the purpose of better understanding how these characteristics enable or interfere with imaging and sonography devices.

Schneditz et al built a sound-speed sensor and evaluated it as a method for measuring total protein concentration. The device is intended to track fluid shifts in a patients blood as they are on a hemodialysis machine. These fluid shifts would manifest themselves as a change in total protein concentration. Schneditz et al investigated the correlation between total protein concentration and speed of sound in order to detect these fluid shifts. Schneditz et al implemented a speed of sound measurement by measuring time of flight along a single direct path. A disadvantage of the Schneditz et al device is that it only works with continuously circulating blood from the patient and back into the patient. The blood must be continuously flowing in order to avoid settling of the blood cells from the plasma, which would cause inaccurate readings. Another disadvantage is that it requires a large volume (60 mL) of blood circulating through tubing from a thermostatted 500 mL bath, and it requires calibration with reference fluids whose speed of sound was known accurately.

The Schneditz et al device was implemented on porcine blood with the white blood cells artificially removed (along with any other blood components in the white blood cell layer). The absence of white blood cells and the physical differences between porcine blood and human blood may significantly alter the ultrasonic response of the blood and therefore the Schneditz et al correlations and methods may not apply to whole or human blood.

Conventional methods for measuring temperature, including thermostat-controlled baths are cumbersome and impractical. Other methods, such as directly contacting the blood with a temperature probe, lead to cleaning and contamination complications. None of the above apparatus or methods solve the problems of speed, accuracy, and portability in hematocrit or hemoglobin concentration measurement. Only the present invention achieves all three goals simultaneously.

SUMMARY OF THE INVENTION

Accordingly, one object of the present invention to provide methods and apparatus for measuring the hematocrit of blood.

It is another object of the present invention to provide methods and apparatus for measuring hemoglobin concentration of blood.

It is another object of the present invention to provide methods and apparatus for measuring mean corpuscular volume of blood.

It is another object of the present invention to provide methods and apparatus for measuring red blood cell count of blood.

It is another object of the present invention to provide methods and apparatus for measuring mean cellular hemoglobin of blood.

It is another object of the present invention to provide methods and apparatus for measuring mean cellular hemoglobin concentration of blood.

It is another object of the present invention to provide methods and apparatus for measuring total protein concentration of blood.

It is another object of the present invention to provide methods and apparatus that will allow simple, accurate, and quick measurements of hematocrit, hemoglobin concentration, mean corpuscular volume, red blood cell count, mean cellular hemoglobin, mean cellular hemoglobin concentration, and/or total protein concentration of blood.

It is another object of the present invention to provide methods and apparatus that can measure the hematocrit of blood to within 2%.

It is another object of the present invention to provide methods and apparatus that can provide a measurement within 30 seconds.

It is another object of the present invention to provide methods and apparatus suitable for a blood draw of less than 10 cc.

It is another object of the present invention to provide methods and apparatus that is battery-operated and small enough to be hand-held.

It is another object of the present invention to provide methods and apparatus that is small enough to be portable.

It is another object of the present invention to provide methods and apparatus that can be easily integrated into a device that measures a variety of other blood properties.

It is another object of the present invention to provide methods and apparatus that can be used for non-invasive in-vivo measurements.

The present inventors have found that the hematocrit (HCT), hemoglobin concentration (HGB), mean corpuscular volume (MCV), mean cellular hemoglobin (MCH), mean cellular hemoglobin concentration (MCHC), total protein concentration (TPC), and red blood cell count (RBC) of blood can be determined accurately using ultrasonic methods.

Accordingly, one embodiment of the present invention provides a means for measuring the properties of blood using ultrasound.

Another embodiment of the present invention provides an apparatus for measuring the properties of blood using ultrasound.

Another embodiment of the present invention provides a method for measuring the properties of blood using ultrasound.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
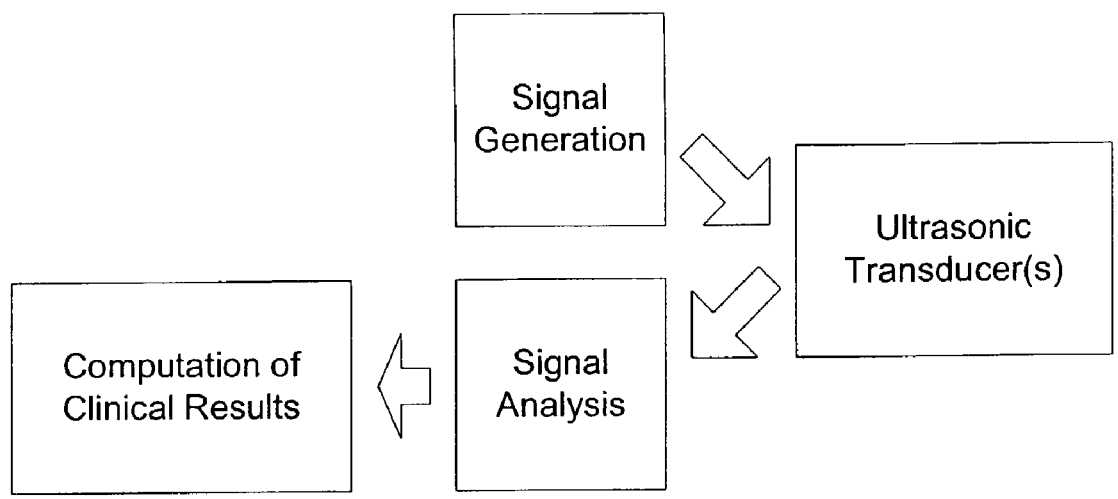
FIG. 1 is a schematic outlining the functions of the electronics stages.

Various other objects, features and attendant advantages of the present invention will be more fully appreciated as the same becomes better understood from the following detailed description of the preferred embodiments of the invention.

Overview

The ultrasonic hematocrit measurement method and apparatus of the present invention can provide measurements of hematocrit, hemoglobin concentration, mean corpuscular volume, red cell count, total protein concentration, mean cellular hemoglobin, and mean cellular hemoglobin concentration that are accurate to within ±2% as verified by the international reference standard, and repeatability, defined as the variability of multiple measurements from the same sample, that varies by not more than 2% of the measured value.

The present invention provides several embodiments for measuring the properties of blood using ultrasound, including but not limited to:

Backscatter—measuring energy reflected from a blood sample

Attenuation coefficient—measuring energy attenuation per unit length through a blood sample Speed of sound—measuring the speed of sound through a blood sample Frequency analysis—measuring the response of the blood chamber to ultrasound at more than one frequency Preferably, the present invention:

Delivers one or more ultrasonic signals to a blood sample

Senses and analyzes the echoed sound

Calculates backscatter coefficients, speed of sound, and attenuation coefficient for frequencies of interest Determines one or more of HCT, MCV, HGB, TPC using the correlations that relate speed of sound, attenuation coefficient, frequency and/or backscatter coefficients to said blood properties. From these results, the values of RBC, MCH, and MCHC are preferably calculated using the definitions RBC=HCT/MCV, MCH=HGB/RBC, and MCHC=MCH/MCV.

One advantage of the present invention, as compared to other devices that measure the blood properties, is that the present invention can be implemented in a portable package and achieves clinically significant improvements of accuracy over other portable devices and the automated cell counters. Furthermore, the invention provides immediate results at the point of care. Lastly, some methods of the invention are suitable for non-invasive, in-vivo measurements (sending ultrasound into the body from outside the skin).

The equipment preferably includes an electronics subsystem and a hardware subsystem. The electronics generate the signal burst and record and analyze the resulting echoes. The hardware contains the sample and maintains alignment of the various components.

Preferably, the present apparatus includes a sample collection mechanism, sample chamber, transducer, transducer coupling to the sample, and automated signal processing.

Principles of Operation

Hematocrit is defined as the volume fraction of red blood cells in a sample of blood. The speed of sound in blood is a direct function of the hematocrit (HCT) and a direct function of the amount of hemoglobin in the blood (HGB). This relationship arises because red blood cells and hemoglobin have different material compositions from the surrounding plasma and therefore different speeds of sound. The speed of sound of whole blood is approximately the bulk average of the speeds of sounds of its components. In other words, the higher the concentration of red blood cells, the more the speed of sound of the blood will approximate that of red blood cells instead of plasma. Because red blood cells make up nearly 50% of the blood volume, HCT and HGB are by far the strongest drivers the speed of sound. Variations of other blood components (white blood cells, platelets, extra-cellular proteins) may change the speed of sound slightly and limit the accuracy of the invention, but their influence is small enough that it has not been identified in experiments to date.

Since the majority of the hemoglobin is in the red blood cells under normal physiological conditions, the HGB and HCT results typically provide equivalent information to the physician. They both indicate the oxygen-carrying capacity of the blood.

$$Cf = g(HCT, T)$$

$$Cf = f(HGB, T)$$

Where:

Cf is the speed of sound in blood, HGB is concentration of hemoglobin, HCT is hematocrit, T is temperature, and f and g are functions that must be determined empirically.

Because speed of sound is a function of HGB and HCT, one can measure speed of sound and apply it as an indication of the HGB and/or HCT by inverting the calculation.

Similarly, the attenuation coefficient in blood is a direct function of the HGB and HCT of the blood because ultrasound attenuates to different degrees in red blood cells than it does in pure hemoglobin or in plasma. This attenuation is caused in part by the viscous losses in the various substances that make up whole blood. The attenuation is also caused in part by the ultrasound scattering off material boundaries such as the walls of red blood cells. For this reason, the attenuation is also a function of the MCV of the blood, although the relationship is weak enough that in some cases it may be neglected.

$$\alpha = f(HCT, MCV, T, F) \sim f(HCT, T, F)$$

Where:
$\alpha$ is attenuation coefficient, HCT is hematocrit, MCV is mean cellular volume, T is temperature, F is frequency, and f is a function that must be determined empirically.

For embodiments in which the relationship between attenuation coefficient and MCV can be neglected without sacrificing excessive accuracy, redundant measurements can be made. Attenuation coefficient and speed of sound can both be used to independently calculate hematocrit and hemoglobin concentration. Then, the two calculations can be compared for error detection and/or averaged to improve accuracy. Alternatively, the two measurements can be used together to eliminate another common variable such as the distance the sound travels in blood or temperature.

Backscatter is the acoustic energy reflected from blood. Since this reflection originates almost entirely from scattering off the red blood cells, the backscattered energy is a complex function of the MCV and HCT of the blood sample. However, the function is only monotonic and well behaved for HCT levels below 15%. Preferably, to use backscattered energy to accurately determine MCV and HCT of a sample, the blood sample first must be diluted to bring the HCT into the linear region below 15% then the device preferably compensates for the dilution in its calculations.

$$Bks = f(HCT, MCV, T, F)$$

Where:
Bks is backscattered energy, HCT is hematocrit, MCV is mean cellular volume, T is temperature, F is frequency, and f is a function that must be determined empirically.

By measuring the ultrasonic backscatter coefficient and using a correlation to HCT, one can determine the HCT of the diluted sample, and thus the hematocrit of the original sample. The backscatter method can also be used in an undiluted sample though the relationship is more complicated. One motivation for measuring backscatter on an undiluted sample is to determine the blood parameters non-invasively by sending and receiving ultrasound into the body.

The backscatter technique and the attenuation coefficient technique of the invention provide good correlations with HCT results. The speed-of-sound technique is more preferable and has demonstrated more accuracy, is more easily implemented, and does not require an independent measurement of MCV or RBC. In contrast, an implementation of the backscatter technique may require a secondary, independent measurement of MCV or RBC.

In one embodiment, the method of the present invention includes subjecting a whole blood sample to one or more ultrasonic pulses, then measuring the ultrasonic characteristics listed above: (a) backscatter from the blood sample, (b) attenuation of the ultrasonic pulse through the blood sample, or (c) the speed of sound through the blood sample. The measurement of (a), (b) or (c) can be used alone or in combination to determine one or more of the related clinical parameters: HCT, HGB, MCV, RBC, MCH, MCHC, TPC.

Speed of Sound Measurement

The preferable way to calculate speed of sound is by measuring the time of flight of short ultrasonic pulses over a known distance.

$$Cf = d/t$$

Where:
Cf is the speed of sound, d is the distance the sound travels through the sample, and t is the measured time it takes for the sound to travel that distance.

The time between send and receive is usually considerably longer than the transit time through the sample because it includes delays in the electronics and delays as the ultrasonic wave passes through materials not being studied such as the container walls. Preferably, the transit time through the sample is not measured directly but instead is determined as the difference between two other measurements: the total transit time (which includes both time in the blood and undesired delays) minus the transit time through only undesired delays.

$$t_{blood} = t_{total} - t_{delays}$$

Where:
$t_{blood}$ is the transit time the ultrasound takes to travel through the sample,
$t_{total}$ is the measured time from send to receive including undesired delays, and
$t_{delays}$ is the measured time of all delays except for the transit through the sample.

Figure 3:
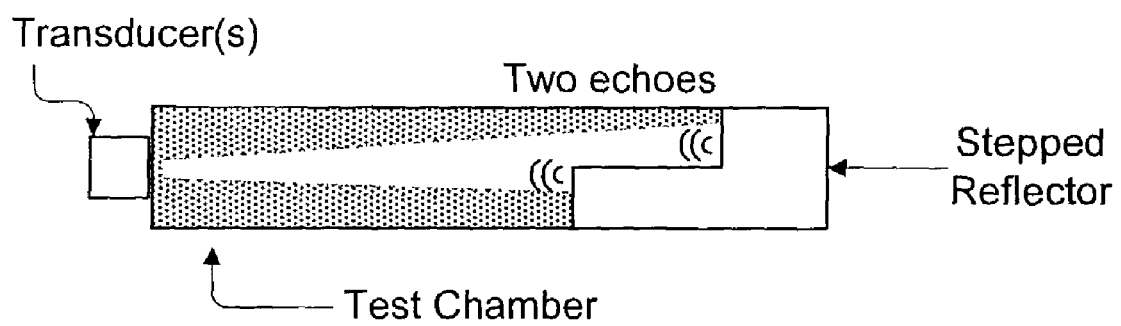
FIG. 3 shows a preferred sample chamber embodiment, which includes a transducer that projects a beam wide enough to reflect off a double step reflector at the other end of the sample chamber. Alternately, a dual element transducer can project two narrow beams through the blood sample, each returning a reflection from a step of the reflector.

One preferable way to measure this time difference is to measure the round trip times of flight from two or more reflectors separated by a known distance along the axis of flight (see FIG. 3). The ultrasound is broadcast in one beam. A portion of the ultrasound echoes from the closer reflector while the rest of the beam continues traveling to echo off the second reflector. The difference between these round trip times, divided by two times the distance between reflectors, is the speed of sound in the sample. Another preferred embodiment of the invention uses a chamber of a precisely known size through which transducers send pulses in pitch-catch mode (see FIG. 8). Using pulse-echo measurements from the edges of the chamber allows the invention to subtract all time delays except the time the sound spent traveling through blood. In another preferable embodiment of the invention, the blood is in a flexible chamber, and time-of-flight measurements are made both before and after deforming the chamber by a known or measurable distance. In one embodiment of the invention, the blood is in a flexible container that fills the space between two precisely located walls. The container material is well controlled such that its time delay is well known and can be subtracted. Preferably, the speed of sound through this flexible wall is roughly matched to the speed of sound through blood, so that the error caused by inaccuracies in estimating the thickness of the wall will negligibly affect the transit time.

Temperature affects speed of sound, attenuation coefficient, and backscatter so the results are preferably adjusted to account for temperature. Furthermore, depending on the materials chosen for the invention, it may need to account for temperature affects on the sizes and shapes of its component parts.

Attenuation Coefficient Measurement

The technique used to measure the attenuation coefficient in blood is similar to the technique used to measure speed of sound. The RMS amplitude of the reflections is measured.

The ratio of the amplitudes from two paths through blood of different lengths is expressed in decibels and divided by the difference of the path lengths.

$$A = 20 \log(V2/V1)/(D2-D1)$$

Where:
A is the attenuation coefficient in dB/in, V2 and V1 are the amplitudes of the two received signals, and D2 and D1 are distances the two signals traveled through the sample.

The speed of sound data and the attenuation coefficient data are typically collected at the same time for each sample. Furthermore, the calculations must be compensated for the temperature of the blood and frequency of the signals.

Backscatter Measurement

The backscatter measurement is performed by analyzing the ultrasonic echo from a diluted blood sample and measuring the RMS voltage of a specified time window within the returned signal. The transducer preferably generates a burst containing 100 cycles of the center frequency of the interrogating transducer. Energy is reflected back from blood-chamber interface, followed immediately by the energy scattered back by the components of the blood sample. By time gating the RMS measurement to measure the energy scattered by only the sample, and averaging over 50 sampled signals or more, the average backscattered power is measured.

Other Ultrasonic Measurements

The invention can also determine the clinical parameters (HCT, HGB, MCV, RBC, MCHC, MCH or TPC) by exciting the chamber with continuous waves. The frequency of this continuous wave is varied slowly to analyze the response of the blood at each frequency. At the resonant frequency, a standing wave is set up which indicates that the wavelength is directly related to the chamber's dimensions. Determining the resonant frequencies allows one to calculate the wavelength and correlate that to hematocrit. Furthermore, the bandwidth (i.e., full width at half-maximum) of the resonant frequency peaks is effectively another indication of attenuation (see, for example, U.S. Pat. No. 5,767,407, the entire contents of which are hereby incorporated by reference). The wider the frequency peak, the higher the attenuation coefficient. Other related ultrasonic measurements that provide similar information include the phase shift or amplitude of the signal.

Acoustic impedance is also an indicator of hematocrit and/or hemoglobin because the acoustic impedance of hemoglobin and other blood constituents is higher than the acoustic impedance of pure plasma. Therefore, higher concentrations of hemoglobin and red blood cells will increase the acoustic impedance of the overall substance from that of pure plasma. Acoustic impedance can be calculated by measuring how much ultrasound is reflected from an interface. If the acoustic impedance of the blood matches the acoustic impedance of the container wall, then no ultrasonic energy will be reflected from the interface. The more the mismatch of acoustic impedances, the more energy will be reflected from the interface. The invention preferably lyses the red blood cells before implementing this method to ensure that the hemoglobin and other blood constituents are evenly distributed throughout the blood and along the material interface being used to measure acoustic impedance.

One final ultrasonic measurement that indicates the physiological parameters is refraction angle. The refraction angle of the ultrasonic wave at a material interface is an indicator of speed of sound as shown by Snell's Law. Therefore, refraction angle will be directly affected by the physiological hematocrit and/or hemoglobin. One preferred way to implement the refraction measurement is to send ultrasound through a triangular blood container that acts as a "prism." The ultrasonic wave enters the blood perpendicular to the container surface. But, because of the triangular shape of the container, the ultrasound strikes the far wall of the chamber at a known angle of incidence. According to Snell's law, the wave will then travel through the container wall at a angle that depends on the speed of sound in the blood. Measuring that angle (preferably using a steered array transducer) allows the invention to back-calculate the speed of sound in the blood use an empirical correlation to calculate the hematocrit and/or hemoglobin.

Snell's Law: $\sin(\theta 1)/C1 = \sin(\theta 2)/C2$

Where:
$\theta 1$ is the angle of incidence, C1 is the speed of sound in material 1,
$\theta 2$ is the angle of refraction, and C2 is the speed of sound in material 2

Electronics

The electronics preferably include means for signal generation, signal capture, and analysis. Preferably, the electronics are responsible for four functions (shown in FIG. 1): generating a precisely controlled signal, sending and receiving the ultrasonic waves, analyzing the received waves, and computing the clinically-relevant results. These functions are divided into the input stage and the receiving stage. Each stage may exist as a separate device, or preferably, some or all of the stages may be integrated together as a single component.

The sending stage preferably includes a programmable signal generator, signal conditioning components (to amplify, filter, and/or reduce noise), and a power amplifier. The signal generator functions to generate one or more acoustic signals. The signals may be a gated sinusoid, square pulse, spike with exponential delay or other function. The signal normally would have a center frequency matched to the center frequency of the transducer in use to maximize the amount of energy delivered to the sample. For frequency sweeps, the frequency range is preferably chosen to lie within the usable bandwidth of the transducer. The pulse generator will preferably generate an electronic pulse to operate the transducers in pitch-catch or pulse-echo mode. The frequency of the signal may be from 1 to 50 Mhz, preferably from 5 to 20 Mhz, depending on the type of measurement being made. Higher frequencies should be chosen if the sound is only traveling a short distance through blood in order to increase time resolution or to achieve wavelengths proximate in length to a red blood cell diameter. Lower frequencies should be chosen for long paths to minimize attenuation. The burst length is more preferably set to 50-200 cycles, most preferably to 100 cycles for backscatter measurements, and 0-5 cycles, most particularly preferably 0.5 cycles for speed of sound and attenuation coefficient measurements. The amplitude of the signal generator is preferably maintained at a setting sufficient to provide high-signal-to-noise ratio.

The signal from the input stage is passed to the transducer. The transducer(s) are preferably high efficiency, single element transducers. A variety of commercially available transducers are suitable for use in the invention. Each transducer may be selected to match the chamber geometry based on the center frequency, bandwidth, focusing, sensitivity, and beam pattern. For backscatter measurements, the range of frequencies is selected to include values both above and below the 15

MHz threshold for Rayleigh scattering. Preferred interrogating frequencies include 6.5, 10, 20, 30, and 40 MHz. In general, higher frequencies are preferable if the sound is only traveling a short distance through blood in order to increase time resolution and narrow the acoustic beam. Lower frequencies are preferable for long paths to minimize attenuation.

For all configurations and measurements, the transducer element diameter is preferably selected to ensure that the beam angles are appropriate for the shape of the chamber. The beam widths should be narrow enough to minimize the chance of undesired sound paths interfering with the measurement. Furthermore, the element diameter affects the distance the transducer must be from the sample (far field distance). Focused transducers may help reduce beam width and far-field distance. Some preferred transducer diameters include 3 mm, 6 mm, and 12 mm. The transducers may be used in pulse echo mode and/or in pitch catch mode depending on how they are arranged relative to the chamber. Measuring the time difference between paths or between these two operating modes can eliminate unknowns such as the delays in the electronics or sample holder.

Figure 4:
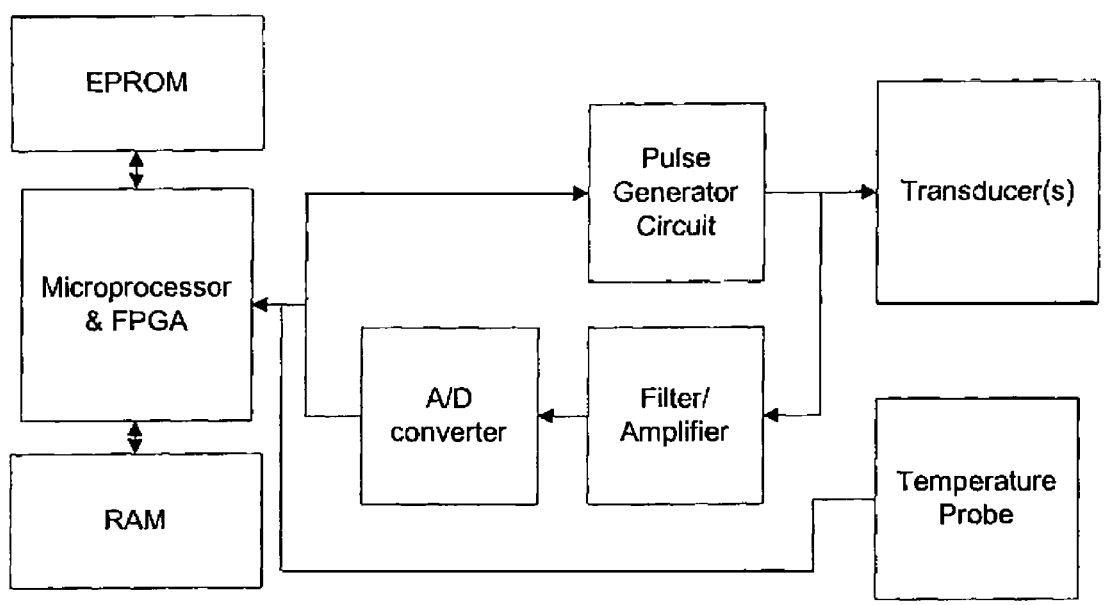
FIG. 4 shows a preferred schematic diagram of the electronics.

The signal returned from the sample causes the transducer to generate an electrical signal that is passed along to the receiving stage. The receiving stage preferably includes signal conditioning, an amplifier, a digitizer, and a means for collecting and analyzing data, such as a microprocessor or microcontroller and RAM, magnetic storage or CD (see FIG. 4). In this configuration, signal measurements and calculations including transit times and amplitude are calculated based on the digitized signal by the microprocessor.

Another preferable receiving stage configuration includes signal conditioning, an amplifier, an analog peak detect circuit and a timing circuit. The peak detect circuit is used to measure the signal peak amplitude and the timing circuit is used to determine the time from signal transmission to receipt.

The amplifier is needed to bring the signal amplitude up to a level that can be readily captured by a digitizer and/or analyzed by analog electronics. Therefore, the amplifier should be chosen to have the needed gain. The amplifier should also be chosen to have the appropriate bandwidth for the planned measurements. The amplifier(s) may also include one or more filters built-in. The filters are used to eliminate noise that lies outside the frequency band being measured. Suitable filters include active and passive filters, RC filters.

The present invention also preferably includes appropriate device control, signal processing and detection logic. Device control may be through an on-board processor, programmable logic controller or through discrete logic blocks. The signal processing algorithms preferably include one or more of the following: analog and digital noise filtering, averaging, gating and automatic gain control. Detection logic preferably includes zero-crossing detection, which automatically measures the exact time a signal crosses zero in order to calculate the transit time of a signal, and amplitude or power measurement.

Hardware

Hardware preferably includes the sample chamber and transducer. The sample chamber or holder is designed to contain the blood sample, allow for stirring of the sample (in the case of backscatter measurements), and maintain alignment and distance between the transducer and the sample. In some embodiments of the invention, the chamber is actually a segment of a tube through which the blood flows continuously (ex-vivo). In other embodiments the chamber is made of flexible materials such as rubber so the blood sample's size or shape can be controlled or adjusted. Alternatively, the blood chamber may comprise the patient's body itself in the case of an in-vivo or non-invasive measurement.

The collection means includes allowances for making live blood draws. The collection method may be an off the shelf syringe, off the shelf lance, or custom device which acts as a collection device and a sample chamber combined. Furthermore, the chamber may be a tube through which the blood flows.

The sample chamber is preferably disposable and compact. Preferred sample chamber materials include glass, polystyrene, polyamide, polyvinylchloride, silicone, polypropylene, latex or polyethylene. The chamber and/or added reflectors (if used) are preferably manufactured to precisely known dimensions so that the sound path length is preferably known to +/−0.2%, more preferably to +/−1-0.05%, which ranges include +/−0.15, 0.125, 0.1, 0.09, 0.075, and 0.065%. A precisely-known path length is preferred to accurately calculate speed of sound from measuring the time of flight. If the chamber cannot be accurately manufactured, then the path length is preferably measured either by the invention itself or by an independent device. The results from said independent device would preferably be fed into the invention automatically by a means such as barcodes.

The sample chamber and/or apparatus parts in acoustic contact with the blood and/or sample chamber preferably has a speed of sound matched to the speed of sound in blood between 1000 m/s and 2500 m/s, which range includes 1200, 1400, 1600, 1800, 2000, 2200, and 2400 m/s. Preferable materials include plastic, rubber, lead, and combinations thereof.

The sample chamber preferably holds 0.05 to 10 mL of blood, which range includes 0.075, 0.1, 0.3, 0.5, 0.7, 0.9, 1, 2, 3, 4, 5, 6, 7, 8, and 9 mL of blood.

The temperature of the sample may be measured directly or indirectly. Indirect means may include waiting for the sample to equilibrate with its environment and measuring the ambient or container temperature in lieu of the blood temperature. If the temperature of the blood is changing rapidly (because it has been freshly drawn for example) repeated ultrasonic measurements allow the invention to infer a trend and predict what the final readings would be once the sample has reached thermal equilibrium with its surroundings. Since speed of sound in any apparatus or container changes with respect to temperature, the temperature of the container walls can be inferred by measuring the speed of sound through the walls. The temperature may also be controlled so that no temperature variations affect the measurement.

The sample chamber and collection means can also be combined into a single component, wherein the blood sample is collected in the collection means, which then acts as the sample chamber upon which the ultrasound method is used. Further, the collection means and sample chamber may comprise a tubular arrangement such that the blood is collected from the patient using a venipuncture needle or other needle device, whereupon the blood flows through a length of tubing. The length of tubing can act as the sample chamber, particularly for the attenuation coefficient and speed of sound measurement methods performed on a sample flowing through the length of tubing. Backscatter based methods are less desirable using a flowing sample due to movement of the red blood cells through the tube. In any event, a calibration can be obtained using samples of independently measured hematocrit, permitting the measurement of the HCT, MCV and/or RBC of the sample, even when flowing through the sample chamber.

One preferred sample chamber embodiment includes a single or dual element transducer that projects beam(s) through the blood sample, returning reflections from a stepped reflector at the other end of the sample chamber (see FIG. 3). The difference in round trip time from these steps can be used to calculate the speed of sound in the test sample.

The stepped reflector design is preferred in that it has no moving parts, and it is not susceptible to variable time delays outside of the sample chamber, such as transducer couplant delay.

Another preferred sample chamber includes a small chamber with rigid parallel walls and a depth such that only a few drops of blood can fill the chamber. Sound is transmitted through the chamber along a path perpendicular to the walls as in FIG. 8.

Another preferred sample chamber consists of a rubber bladder. This is configured such that when it is placed in the electronics unit and filled with blood, it expands to fill the space between a single fixed transducer and a reflector or between two fixed transducers in the electronics unit.

Other preferred sample chambers include capillary tubes, sample cards, and those that include integral disposable transducers. The capillary tubes are preferably capped at one end. This type of tube is similar or identical to that currently used in medical settings as part of a micro-hematocrit test known to those of skill in the art. The sample card collects a drop of blood in a flat, wide sample chamber. The sample card optionally includes a thumb tab to provide a landing for the users fingers.

The reflector could be inside the chamber or outside. Most preferably, the chamber shape itself would act as the reflector for ease of manufacturing. The material of the reflector is not particularly limited. The path length difference is likewise not particularly limited, and could preferably range from 1 mm to 10 cm, which range includes 2, 3, 4, 5, 6, 7, 8 and 9 mm, and 1, 2, 3, 4, 5, 6, 7, 8, and 9 cm. Longer paths are preferred for making a more accurate measurement, but shorter paths require less blood. Moving reflectors are possible. In all configurations, vertical ultrasound paths are preferred so that if the red blood cells settle, their concentration in the beam remains constant. In the case of a horizontal beam, the cells could settle preferentially into or out of the beam causing an erroneous reading. Or, different portions of the beam could pass through different concentrations of cells causing a distorted answer. In the same way, a vertical sound path ensures that even if thermal stratification occurs, the ultrasound will travel through all the temperature layers of the blood instead of preferentially measuring through a warmer or colder region. The transducers may use liquid or grease as an acoustical couplant to a solid blood container, may be coupled directly to the sample container (dry coupled), or may transmit sound directly into liquid or gas instead of a solid. The transducers may be held in a fixture to ensure reliable acoustical coupling to the sample. In one preferred embodiment, the transducers are disposable and built into the sample chamber. When disposable transducers are integrated into a disposable chamber, the chamber is preferably connected to the test device electrically instead of acoustically.

The transducers are preferably narrow beam width and more preferably focused to avoid coherent noise caused by stray reflections depending on the geometry of the sample chamber. Preferably, transducers having center frequencies of approximately 1 MHz to 50 MHz, more preferably 5 to 20 MHz may be used. 20 MHz transducers are most preferred, however. The higher frequency transducers accommodate a shorter path length and more precise timing. A pair of transducers are most preferably used, one on each side of the collected sample as in FIG. 8.

The hardware may include means for user interface and device packaging. The transducer and sample chamber configuration may be integrated into a portable, battery powered, self-contained device. Other embodiments of the invention include integrating the present invention as a subsystem in a device that performs other tests or functions.

Preferred hardware sub assemblies include:
the case,
the display,
the transducers,
the sample holder,
the chamber,
user buttons,
power system, and
circuit board.

The invention is particularly suitable for handheld or portable application, but it is also suitable for use in tabletop or permanent installations.

Particularly preferred embodiments of the present invention device are given below:

Preferred Embodiment A

One preferred embodiment (A) includes a handheld device suitable for use with a drop of blood and using one or more permanent transducers. In this embodiment, described below, the user draws a drop of blood from the patient via a finger or heel stick and collects it in a small sample chamber (e.g., tube, sample card). The sample is placed into the device and the device will display the hematocrit, the hemoglobin content, red blood cell count, the mean cellular volume, the mean cellular hemoglobin, the mean cellular hemoglobin concentration, and/or total protein concentration. This embodiment is preferably handheld, battery powered, and portable. The sample chamber is preferably disposable.

Test Chamber

Three types of test chamber are preferable for this device and they all use a drop or several drops of blood. The fact that they use a few drops of blood limits the size of the chamber accordingly. The first will be a small capillary tube, preferably capped at one end. This type of tube is similar or identical to that currently used in medical settings as part of a micro-hematocrit test known to those of skill in the art. The second preferred embodiment is a sample card, which collects a drop of blood in a small rectangular hole to through which ultrasonic measurements can be made. The sample card optionally includes a thumb tab to provide a landing for the users fingers. This type of sample card is also known to those of skill in the art and is not particularly limited. The third preferred embodiment is a sample card, which collects a drop of blood in a flexible thin walled chamber that fills the space between two precisely-located walls within the meter.

Transducer

Figure 8:
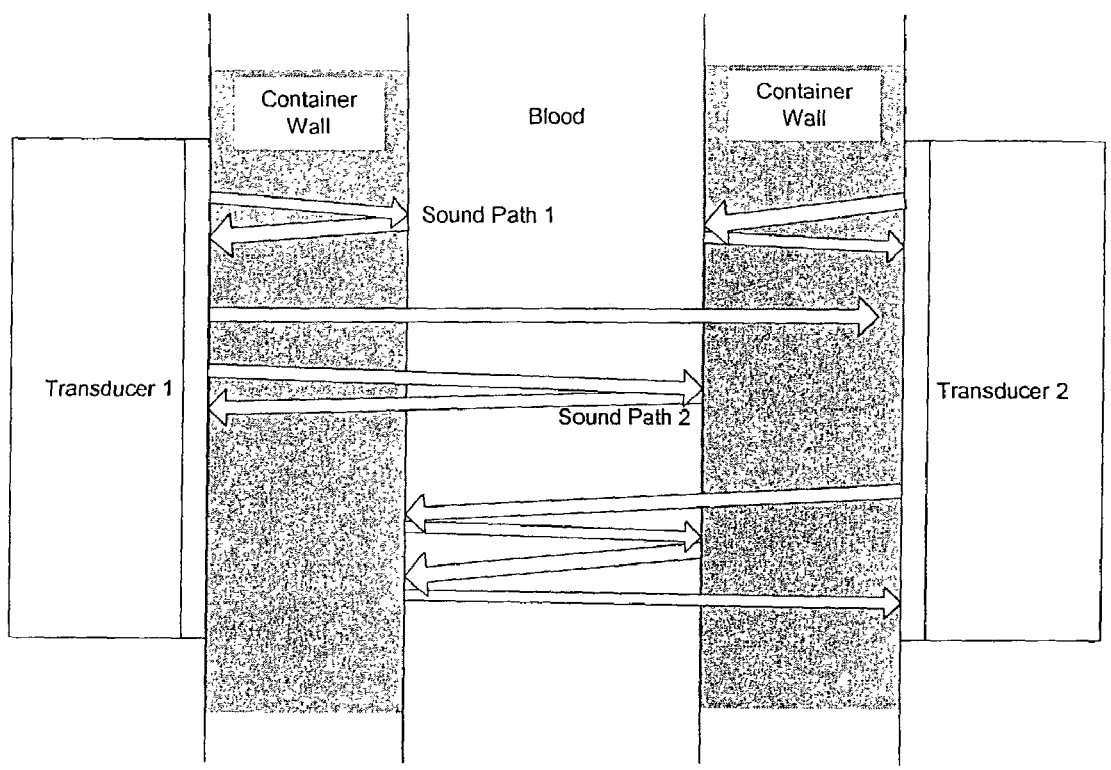
FIG. 8 shows a preferred embodiment of the blood container in which two transducers are mounted on opposite sides of the blood. A few examples of the many paths taken by the ultrasonic wave are shown schematically. Received ultrasound may be analyzed from one or multiple paths in order to calculate the medical results.

The transducers in this preferred embodiment are preferably in the 10 to 100 MHz range, more preferably 20 MHz. Though the measurement can be made with only one transducer, a pair is most preferably used, one on each side of the collected sample. Locating the pair in this fashion allows both pitch-catch and pulse-echo signals to be measured as shown in FIG. 8. The fixture holding these transducers preferably ensures reliable acoustic coupling between the sample chamber and the transducers.

Signal Generator

The signal generator generates a simple electronic signal of sufficient duration and amplitude to operate the transducers. The frequency of the signal is appropriate for the selected transducer, and is preferably from 0.25 to 3 cycles in length. The amplitude of signal should be as high as possible without exceeding the transducers' ratings. Another amplifier circuit may be needed to maximize the signal-to-noise ratio. With the appropriate electronics (discussed above) this hardware can also determine the relevant clinical parameters using other measurements such as measuring the frequency response of the chamber to determine how much it resonates at each frequency.

Device Control, Signal Processing, Detection Logic

Device control may be through an on-board processor, or through a programmable logic controller. The signal processing algorithms preferably include one or more of the following: noise filtering, averaging, and automatic gain control, which are understood by one of ordinary skill in ultrasonics or electrical engineering, and which are not particularly limited. Detection logic preferably includes zero-crossing detection. Zero-crossing detection is a method for accurately measuring the time at which a signal like a wave burst arrives. In this method, the wave is timed by detecting precisely when the signal crosses zero. Because most typical bursts last several cycles and therefore cross zero multiple times, a single crossing is preferably used consistently in a given application of the method. For example, one embodiment is to use the $2^{nd}$ (or $3^{rd}$ or $5^{th}$) zero crossing of every burst as the consistent timing point.

Case and Display

The case will preferably accommodate the sample chamber, the transducers, a display, and supporting electronics.

Communications

One or more interfaces are preferably included to communicate with other medical equipment, with a hospital device network, or both.

Preferred Embodiment B

Another preferred embodiment (B) provides a handheld device suitable for use with a drop of blood and uses disposable transducers. Like embodiment (A), this embodiment, described below, includes a handheld device and will measure hematocrit, the hemoglobin content, and/or the other red blood cell indices. Unlike embodiment (A), though, embodiment (B) preferably includes disposable transducers, which are preferably integrated into the sample chamber.

Test Chamber

The test chamber of this embodiment may be in either format described in Embodiment (A) with the exception that the test chambers in Embodiment (B) preferably include one or two disposable transducers built into the test chamber. This chamber with would then use an electrical connection to the test device instead of acoustic coupling. These disposable transducers may be preferably manufactured using micromachined capacitive elements (MEMS) to minimize cost.

Disposable Transducers

The disposable transducers are preferably in the 10 to 100 MHz range, more preferably 20 MHz. A pair of these transducers is preferably used, one on each side of the collected sample. These disposable transducers may or may not be in contact with the drawn blood sample.

Other Elements

The other elements are the same as those described in Embodiment (A).

Preferred Embodiment C

Another preferred embodiment (C), described below, provides a handheld device suitable for use with a tube of blood and using permanent transducers. This embodiment varies from (A) and (B) in that a larger volume of blood is used. In this embodiment, the user draws a tube of blood from the patient via venipuncture. The sample is placed into the device and the device displays the hematocrit, the hemoglobin content, and/or the mean cell volume. The device is preferably handheld, battery powered, and portable. The sample chamber is preferably disposable.

Test Chamber

The test chamber is a standard medical tube. The tube is inserted into the invention and the transducers couple directly to its outside surface. Two modes of signal propagation are preferable. In the first, the signals are transmitted perpendicularly to the tube axis and transmit through the tube for pitch-catch measurements and reflect off the walls for pulse-echo measurements as shown in FIG. 8. In the second mode, the signal travels along the axis of the tube or perpendicularly but reflect from a disposable, two-step reflector of known size that has previously been inserted into the tube as shown in FIG. 3.

Other Elements

The other elements are the same as those described in Embodiment (A).

Preferred Embodiment D

In this preferred embodiment, the present invention functions as described above and it is integrated into a device that performs other blood tests. In this case, the details of the sample chamber and transducer configuration may resemble the embodiments described above but must also be chosen to work with the other blood tests being performed.

Preferred Embodiment E

In this final preferred embodiment, the measurement is made in-vivo, without drawing any blood from the patient. The device is held against the patient's skin and sends ultrasound into the patient. The backscatter, speed of sound, attenuation, and other ultrasonic measurements are calculated from the received signals and used to infer the blood properties.

Test Chamber

In this embodiment, the test chamber is the patient's body.

Transducer

An array transducer is preferable so that the device can dynamically steer the sound beam and alter the focus length to search for a large artery or vein.

Signal Generator

If an array transducer is chosen, an appropriate signal generator would have to be chosen to control the array and allow the beam-steering.

The other elements of this embodiment are preferably similar to previously described embodiments.

Other preferred embodiments A-TTT are given below. These preferred embodiments may each independently be combined with any method and/or apparatus described herein.

A. The apparatus and method, wherein the sample chamber includes a stepped reflector.
B. The apparatus and method, wherein the stepped reflector includes 2 or more stepped reflective surfaces.
C. The apparatus and method, wherein the sample chamber includes one or more reflectors for reflecting the signals to at least one of the transducers.
D. The apparatus and method, further including one or more acoustic couplants sonically connecting the transducers and the blood.
E. The apparatus and method, further including a means for measuring backscatter of the ultrasonic pulses from the blood.
F. The apparatus and method, further including a means for measuring speed of sound through the blood.
G. The apparatus and method, further including a means for measuring pulse attenuation through the blood.
H. The apparatus and method, wherein at least one of the transducers has a center frequency of from 5 to 100 MHz.
I. The apparatus and method, wherein the transducers is a pair of opposed transducers, wherein each of the opposed transducers is located on opposite sides of the sample chamber.
J. The apparatus and method, further including a case containing the sample chamber, the transducers, and a power supply, and having thereon a display and one or more user buttons.
K. The apparatus and method, wherein the transducers operate in pitch-catch mode with a pulse of from 1 to 100 cycles in length.
L. The apparatus and method, wherein the transducers are disposable transducers.
M. The apparatus and method, wherein the transducers are disposable transducers and are integrated into the sample chamber and are in contact with the blood.
N. The apparatus and method, wherein the sample chamber is substantially acoustically transparent.
O. The apparatus and method, wherein the apparatus is portable.
P. The apparatus and method, wherein the apparatus is handheld.
Q. The apparatus and method, wherein the blood is human blood.
R. The apparatus and method, wherein the blood is whole blood.
S. The apparatus and method, wherein the blood is not circulated.
T. The apparatus and method, wherein 10 drops or less of blood are used.
U. The apparatus and method, wherein 50 mL or less of blood is used.
V. The apparatus and method, wherein 500 mL or less of blood is used.
W. The apparatus and method, wherein the blood is not permanently affected by the measurement.
X. The apparatus and method, wherein the blood is not diluted.
Y. The apparatus and method, wherein the blood is diluted.
Z. The apparatus and method, further including a means for measuring the temperature of the blood.
AA. The apparatus and method, wherein temperature is not measured.
BB. The apparatus and method, wherein the temperature is measured directly.
CC. The apparatus and method, further including a means for controlling the temperature.
DD. The apparatus and method, wherein the temperature of the blood is controlled or known.
EE. The apparatus and method, further including a means for displaying a measurement of the HCT, HGB, MCV, RBC, MCHC or MCH of blood within 2 minutes.
FF. The apparatus and method, further including a means for making one or more additional measurements on the blood.
GG. The apparatus and method, wherein the chamber is a closed volume.
HH. The apparatus and method, wherein the chamber is flexible.
II. The apparatus and method, wherein the chamber is non-flexible.
JJ. The apparatus and method, wherein the chamber is disposable.
KK. The apparatus and method, wherein the chamber has an acoustic impedance that is matched or not matched with an acoustic impedance of the blood.
LL. The apparatus and method, further including a means for the blood to flow through the chamber.
MM. The apparatus and method, further including a means for analyzing a reflected ultrasound.
NN. The apparatus and method, wherein a combination of transmitted and reflected signals are used to make the measurement.
OO. The apparatus and method, wherein reflected ultrasound is analyzed to separately determine transit time in blood and eliminate other delays.
PP. The apparatus and method, wherein the ultrasonic signal is above 3 Mhz.
QQ. The apparatus and method, wherein the ultrasonic signals are long pulses or waves.
RR. The apparatus and method, wherein the speed of sound is measured by exciting the blood with a plurality of frequencies and determining at least one or more frequencies at which there is peak resonance.
SS. The apparatus and method, wherein ultrasonic attenuation is measured.
TT. The apparatus and method, wherein ultrasonic backscatter is measured.
UU. The apparatus and method, wherein the blood is diluted in order to use a monotonic correlation to determine results from the measurement of backscatter.
VV. The apparatus and method, wherein ultrasonic frequency response is measured.
WW. The apparatus and method, wherein ultrasonic phase is measured.
XX. The apparatus and method, wherein ultrasonic amplitude is measured.
YY. The apparatus and method, wherein a movable reflector is used to reflect sound to at least one of the transducers.
ZZ. The apparatus and method, wherein reflections are detected from multiple surfaces.
AAA. The apparatus and method, further including a means for determining a transit time by directly measuring a time from transducer excitation to a time of detection of a received signal.
BBB. The apparatus and method, further including a means for measuring ultrasonic speed of sound.
CCC. The apparatus and method, further including a means for measuring ultrasonic time of flight.
DDD. The apparatus and method, which includes only a single transducer.
EEE. The apparatus and method, which includes more than one transducer.
FFF. The apparatus and method, which includes composite transducers or array transducers.
GGG. The apparatus and method, wherein the transducers are not mounted directly across from each other.

HHH. The apparatus and method, wherein the transducers are acoustically coupled without a liquid couplant.

III. The apparatus and method, wherein more than one signal is used in combination to eliminate delays or transit times through other materials from the calculation of transit time through blood.

JJJ. The apparatus and method, wherein ultrasonic characteristics are used in combination to eliminate an unknown variable such as the distance ultrasound travels in blood or the temperature.

KKK. The apparatus and method, wherein one or more ultrasonic reflections are measured.

LLL. The apparatus and method, wherein a stepped reflector returns multiple ultrasonic reflections.

MMM. The apparatus and method, wherein the apparatus or chamber comprises a material with speed of sound matched to the speed of sound in blood—between 1000 m/s and 2500 m/s such as plastic, rubber, and lead.

NNN. The apparatus and method, wherein the blood is diluted in order to use a monotonic correlation between backscatter and the measured properties.

OOO. The apparatus and method, wherein the means for containing blood includes the body itself and the measurement is taken in-vivo, either invasively or non-invasively.

PPP. The apparatus and method, further including a means for measuring the properties of blood using ultrasound backscatter, which includes measuring energy reflected from blood.

QQQ. The apparatus and method, further including a means for measuring the properties of blood using ultrasound attenuation, which includes measuring energy attenuation through blood.

RRR. The apparatus and method, further including a means for measuring the properties of blood using using ultrasound speed of sound, which includes measuring the speed of sound through blood.

SSS. The apparatus and method, further including a means for measuring the properties of blood using an ultrasound frequency sweep, which includes measuring resonance frequencies of blood and the bandwidth of each resonance.

TTT. The apparatus and method, further including a means for measuring the properties of blood using using an ultrasound pulse of combined frequencies, and resolving the combined frequencies with Fourier transform methods.

The entire contents of each of the following references are hereby incorporated by reference:

Edwin L. Carstensen, Kam Li, and Herman P. Schwan, "Determination of the Acoustic Properties of Blood and its Components," The Journal of the Acoustical Society of America Volume 23, Number 2, Pages 286-289 (1953).

Edwin L. Carstensen and Herman P. Schwan, "Absorption of Sound Arising from the Presence of Intact Cells in Blood," The Journal of the Acoustical Society of America Volume 31, Number 2, Pages 185-189 (1959).

Rubens A. Sigelmann and John M. Reid, "Analysis and Measurement of Ultrasound Backscattering from an Ensemble of Scatterers Excited by Sine-Wave Bursts," The Journal of the Acoustical Society of America Volume 53, Number 5, Pages 1351-1355 (1973).

KoPing K. Shung, Rubens A. Sigelmann, and John M. Reid, "Scattering of Ultrasound by Blood," IEEE Transactions on Biomedical Engineering Volume BME-23, No. 6, Pages 460-467 (1976).

Stephen E. Borders, Arnost Fronek, W.Scott Kemper and Dean Franklin, "Ultrasonic Energy Backscattered from Blood," Annals of Biomedical Engineering, Volume 6, pages 8392 (1978).

S. Xu and H. Ermert, "Models for Describing the Scattering of Ultrasound in Blood," Biomed. Technik, Volume 42 (5), Pages 123-131 (1997).

S. A. Gross, R. L. Johnston, and F. Dunn, "Comprehensive Compilation of Empirical Ultrasonic Properties of Mammalian Tissues," J. Acoust. Soc. Amer., Vol. 64, Pages 423-457, 1987.

Larry Y. L. Mo and Richard S. C. Cobbold, "A Stochastic Model of the Backscattered Doppler Ultrasound from Blood," IEEE Transactions on Biomedical Engineering, Volume BME-33, No. 1, Pages 20-27 (1986).

I. Y. Kuo and K. K. Shung, "High Frequency Ultrasonic Backscatter from Erythrocyte Suspension," IEEE Transactions on Biomedical Engineering, Volume 41, No. 1, Pages 29-33 (1994).

Daniel Schneditz, Thomas Kenner, Helmut Heimel, and Hans Stabinger, "A soundspeed sensor for the measurement of total protein concentration in disposable, blood-perfused tubes," J. Acoust. Soc. Am., Vol. 86, No. 6, Pages 2073-2080 (1989).

K. Kirk Shung, Guy Cloutier, and Chee C. Lim, "The Effects of Hermatocrit, Shear Rate, and Turbulence on Ultrasonic Doppler," IEEE Transactions on Biomedical Engineering, Volume 39, No. 5, Pages 462-489 (1992).

U.S. Pat. No. 5,767,407.

EXAMPLES

Having generally described this invention, a further understanding can be obtained by reference to certain specific examples which are provided herein for purposes of illustration only and are not intended to be limiting unless otherwise specified.

Experimental Apparatus

Figure 2:
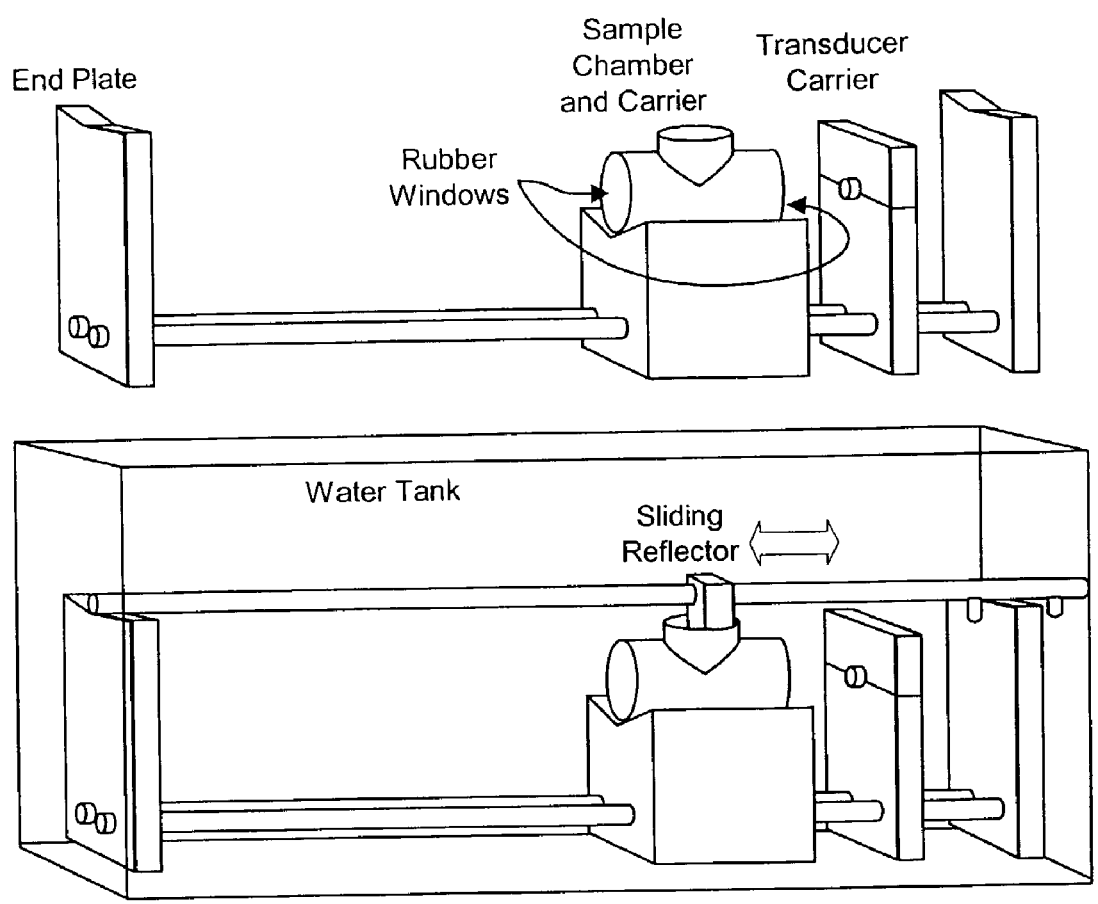
FIG. 2 shows an embodiment of the invention that was used as an experimental apparatus to test the feasibility of measuring blood properties using ultrasound, which includes sample fixture having two rails that act as guides for the end plates, transducer carriers, reflector, and sample chamber.

An immersed transducer and sample arrangement was built (see FIG. 2). This configuration included a water bath, immersed transducer, reflector, and sample. The sample was contained in the blood chamber, which was designed with stretched latex "windows" to contain the blood and to reduce ultrasonic refection from the wall of the sample. Water in the bath acted as an effective and inexpensive waveguide and couplant. Other couplant means and sample chamber means are also suitable.

Figure 6:
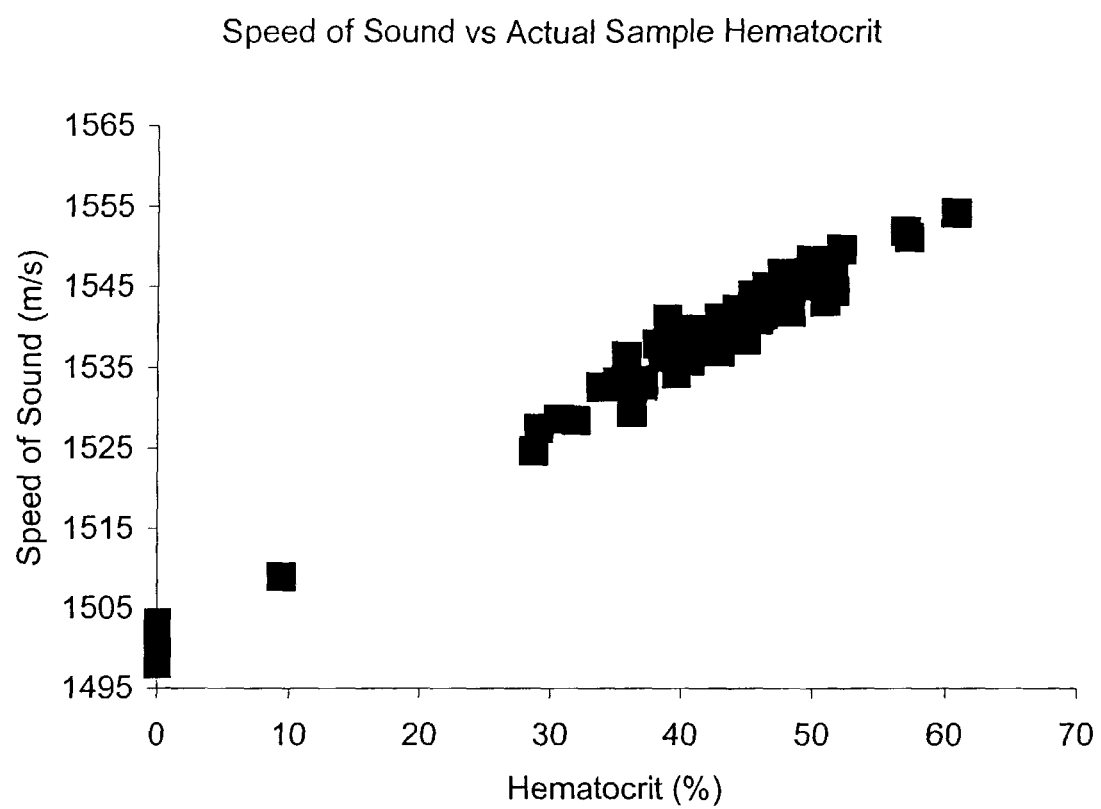
FIG. 6 shows the preliminary speed of sound results

Most of the testing focused on the speed of sound-HCT and attenuation coefficient-HCT correlations in the physiological hematocrit range because they were the easiest to implement. Correlations were also developed against HGB and potential interfering factors. FIG. 6 is a graph of the speed of sound data collected (sample size 65). A linear correlation between speed of sound and hematocrit was expected. The linear correlation coefficient for this set of data is 0.990, supporting the strong correlation.

Figure 7:
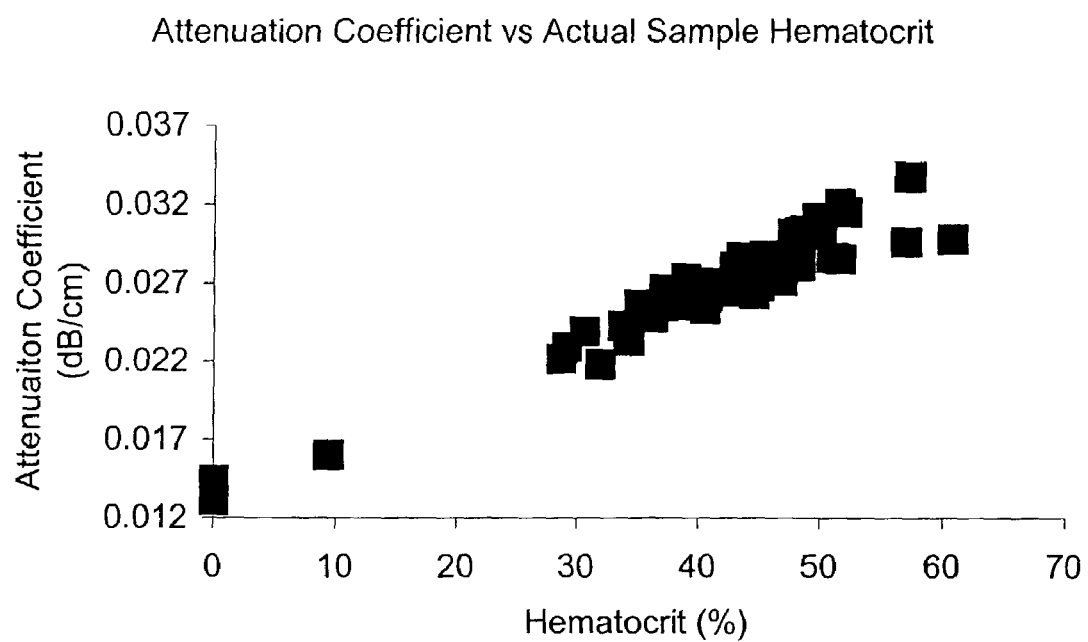
FIG. 7 shows the preliminary attenuation results

FIG. 7 is a graph of the attenuation coefficient data collected (sample size 65). These data points have also been corrected for RBC preservative type. An approximately linear correlation between attenuation coefficient and hematocrit was expected. The linear correlation coefficient for this set of data is 0.975. Once again, it is likely that some of the scatter is caused by variations in the MCV of the samples, but limitations in the sample size and scatter in the data prevent establishing a statistically significant correlation with MCV.

Figure 5:
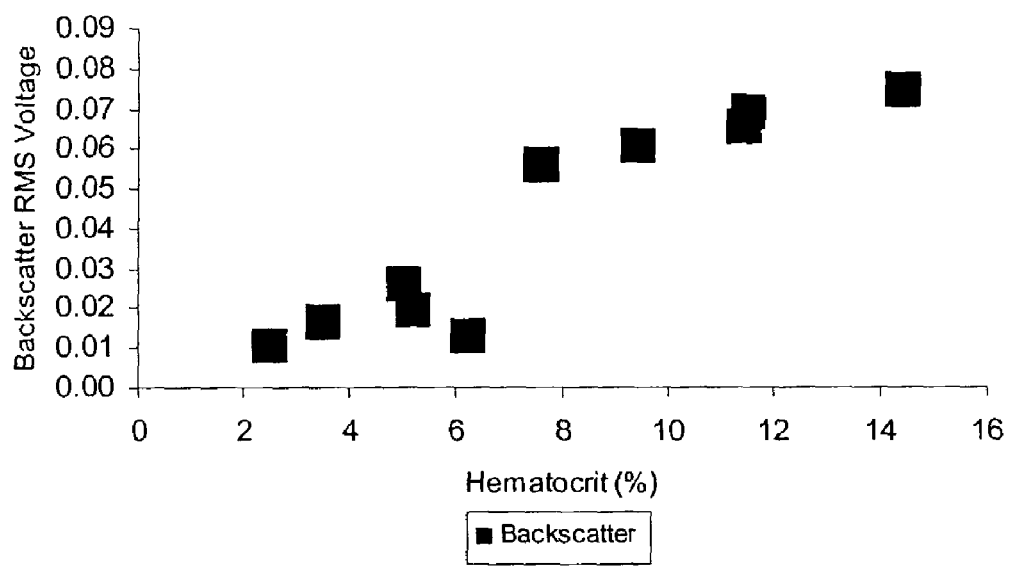
FIG. 5 shows the preliminary backscatter results

Backscatter results are illustrated in FIG. 5 (sample size 10). The points shown are from 0% to 15% HCT. In this region, the data should be linear. The straight line correlation is 0.932. This suggests that a good correlation was identified between backscatter and HCT but not as strong as with speed of sound or attenuation.

After correction for temperature and preservative, the results were analyzed using a reverse linear regression. Using this linear regression, the accuracy of predicting HCT, hemoglobin concentration (HGB), and red cell count (RBC) given speed of sound and attenuation coefficient was calculated with a 90% confidence interval. The results demonstrated that accurate correlations relating speed of sound to HCT and to HGB as well as correlations relating attenuation coefficient and backscatter to HCT and to HGB were developed. Sources of experiment error have been identified which can be substantially reduced, resulting in significant accuracy improvements. Table 1 summarizes the correlation accuracies achieved and the expected accuracy with improved experimental process.

TABLE 1

Correlation Uncertainties

| Measure Parameter | Demonstrated Accuracy (95% Confidence Interval) | | Expected Accuracy (95% Confidence Interval) | |
| --- | --- | --- | --- | --- |
| | Speed of Sound | Attenuation Coefficient | Speed of Sound | Attenuation Coefficient |
| HGB (% of reading) | 5.5% | 20% | 1.0% | 1.0% |
| HCT (% of reading) | 3.0% | 11% | 1.0% | 1.0% |
| RBC (% of reading) | 9.9% | 15% | 1.4% | |

*The expected accuracy of RBC assumes that both speed of sound and attenuation are simultaneously measured and used to calculate HCT and MCV. The RBC can be calculated more accurately in this situation because the MCV it uses is a calculated value instead of an assumed value.
Known significant sources of error affecting the accuracy of the correlations include:
inaccuracy of the reference cell counter (claimed +/−2%)
dimensional precision of the test fixture,
variation in the actual amount and type of preservative in the blood samples,
the accuracy of the temperature correction,
the age of the expired blood samples, and Since the reference cell counter was the only source of comparison for blood parameters, and because it claims a repeatability of no better than 2%, this was one of the driving sources of scatter between the ultrasonic measurements and the reference blood parameters. Assuming that the errors of the automated counter are uncorrelated with the errors of the present invention, the 3% error identified between the two devices would indicate that the present invention is actually achieving 2% accuracy relative to an absolute reference standard. This assumption suggests that the remainder of the error is introduced by the automated counter which claims to performing no better than the present invention. The other sources of error listed above are all plausible drivers of error. An upgraded apparatus (higher precision in dimensional accuracy and temperature measurement) testing fresh blood without preservatives and compared against multiple references (including the international reference standard) will likely demonstrate an accuracy of +/−1% of reading.

Experiment Conclusions

Excellent correlations were developed relating HCT to speed of sound and attenuation coefficient, and relating HGB to speed of sound and attenuation coefficient. The goal of developing an HCT and HGB measurement method suitable to an accurate, portable, rugged device has been met with resounding success.

The method of the invention has a ±3.0% accuracy for estimation of hematocrit by speed of sound (relative to an automated cell counter). Using fresh blood samples, two of the known significant error sources, preservative and sample age, would be eliminated. The accuracy of the final device is expected to be within 1% of the value measured by reference standards. Similar accuracies can be achieved based on the attenuation coefficient correlations. The invention device is significantly more accurate than any other portable HCT meter.

With the present invention, accurate hematocrit and hemoglobin concentration measurements are provided with a turn-around time of just one minute, more than a 90% reduction in time from sample to results. Simple and accurate HCT and HGB measurements are thus available without the wait. The present invention is useful in both civilian and military emergency medical environment. The present invention can be implemented as a small, lightweight, self-contained, and durable so that it may be readily carried to the scene of an emergency. The present invention is fast and easy to use in adverse conditions. Most importantly, it is accurate, so that emergency medical personnel can act with confidence and provide useful information as the patient is transferred to an emergency room.

The present invention also serves the private practice physician. The device provides an alternative to contract blood analysis laboratories when results are needed immediately. The speed and accuracy of the device provides physicians with information that they can use during the same visit, saving time on follow-up visits and telephone calls.

Table 2 below compares some advantages of the present invention with commercially available hematocrit and hemoglobin devices.

TABLE 2

Comparison of some advantages of present invention to commercially available hematocrit and hemoglobin devices.

| Technique | Typical Accuracy (± % of reading, 95% confidence interval) | Portable | Turnaround at POC (estimated minutes) | Current And Potential Markets | Drawbacks |
| --- | --- | --- | --- | --- | --- |
| Centrifuge | 2-5 | No | 5-30 | Private Practice Offices | Slow, and accuracy depends on operator skill |
| Cell Count-Auto | 2-3.5 | No | 30+ | Hospitals | Expensive, not portable |
| Optical | 6 | No | 1 | Cardiac OR | Needs blood circuit to operate |

TABLE 2-continued

Comparison of some advantages of present invention to commercially available hematocrit and hemoglobin devices.

| Technique | Typical Accuracy (± % of reading, 95% confidence interval) | Portable | Turnaround at POC (estimated minutes) | Current And Potential Markets | Drawbacks |
|---|---|---|---|---|---|
| Electrical (conductivity) | 6 | Yes | 1 | Hospitals, Private Practice Offices | Screening only |
| Photometric | 3 | Yes | 1 | Hospitals | Screening only, HCT measures hemoglobin not hematocrit |
| Ultrasonic (Present invention) | 1-2 | Yes | 1 | Hospitals, EMS, Private Practice Office | None |

The present invention is a significant improvement over conventional devices in each of the following areas:

Portability—the components in the device are small, durable, and lightweight. Target weight is less than 10 pounds, which is less than one third of the weight of automated cell counters.

Speed—A single ultrasonic pulse and measure cycle takes fractions of a second and firmware signal analysis would allow nearly instantaneous results. Target cycle time is less than 60 seconds, which is a 90% improvement over the minimum 10 minutes required for processing by a blood lab.

Accuracy—two-times better than existing portable devices. Target accuracy is better than ±1%.

There are other numerous distinctions and improvements in the present invention over conventional ultrasonic systems. The present invention is applicable to measuring not just TPC, but also HCT, HGB, RBC, MCV, MCHC, and MCV. To implement these multiple measurements, the present invention preferably utilizes not just speed of sound but a variety of ultrasonic measurements including time of flight, attenuation, backscatter, continuous wave response, frequency response and refraction. Whereas Schneditz et al implemented a speed of sound measurement by measuring time of flight along a single direct path (no reflections), multiple echoes and paths may be analyzed in combination in the present invention. One embodiment of the present invention desirably utilizes multiple characteristics (such as speed of sound and attenuation) in combination to eliminate uncontrolled variables such as distance or temperature.

Another advantage of the present invention is that it can be applied to in-vivo or non-invasive measurements by sending ultrasound through the skin. The particularly suitable embodiments of the invention for this application include but are not limited to the backscatter method or the method of subtracting the times of flight of multiple echoes to eliminate delays due to traveling through skin, fat, or blood vessel walls.

Advantageously, the present invention is not limited to only continuously circulating blood from and to the patient. The present invention is also suitable for using stationary blood.

Where appropriate, the present invention does not require a large volume of blood. It is suitable for use with 0.05 mL or less (1 drop) whereas, for example, the Schneditz et al device uses an estimated 60 mL of blood circulating through the tubing from a 500 mL bath. This is a quantum leap in scale (a factor of 100-1000 in volume). Other embodiments of the invention desirably avoid the problems associated with conventional methods for measuring temperature, such as thermostat-controlled baths, which are cumbersome and impractical, and direct contact of the blood with a temperature probe, which leads to cleaning and contamination complications. Where appropriate, the present invention allows for the automatic measurement of temperature using, for example, ultrasonic measurements of the container, estimating temperature based on asymptotic trends of results, or measuring the temperature of the blood's surroundings, and designing the apparatus to quickly approach thermal equilibrium.

Having now fully described this invention, it will be apparent to one of ordinary skill in the art that many changes and modifications can be made thereto without departing from the spirit or scope of the invention as set forth herein.

The invention claimed is:

1. A method for measuring one or more of HCT, HGB, MCV, RBC, MCHC, or MCH of blood, comprising:
   collecting a sample of blood of 1 mL or less in a spatially defined disposable sampling device having at least one known dimension of length, said sample being contained within said disposable sampling device;
   inserting said disposable sampling device in an analyzer;
   sending one or more ultrasonic signals into said blood sample while still contained within said disposable sampling device;
   measuring one or more characteristics of at least one ultrasonic signal received from the blood sample, said one or more characteristics of the at least one ultrasonic signal being selected from the group consisting of time of flight, amplitude and backscatter energy;
   calculating from said one or more measured characteristics of said at least one ultrasonic signal one or more characteristics of said blood sample, said characteristics of said blood sample being selected from the group consisting of the speed of sound through said blood sample, the attenuation coefficient of said blood sample and the backscatter coefficient of said blood sample; and
   determining at least one property of said blood sample from said calculated one or more characteristics of said blood sample, said property being selected from the group consisting of HCT, HGB, MCV, RBC, MCHC, MCH, and combinations thereof of the blood.

2. The method of claim 1, wherein the received ultrasonic signal comprises at least one selected from the group consisting of signals received from two or more acoustic paths, signals received from more than one reflective interface, and a combination thereof.

3. The method of claim 2, wherein said signals are used in combination to eliminate one or more delays or transit times through one or more other materials from the calculation of transit time through blood.

4. The method of claim 1, further comprising the step of measuring the temperature of said blood sample, and
wherein said calculating step further comprises utilizing at least two characteristics selected from the group of consisting of said measured characteristics of said at least one ultrasonic signal received from the blood sample and said temperature of said blood sample to eliminate at least one uncontrolled variable selected from the group consisting of a distance traveled by said one or more ultrasonic signals sent into said blood sample, a temperature of said blood sample, and a combination thereof.

5. The method of claim 1, wherein one or more ultrasonic signal reflections are measured.

6. The method of claim 1, wherein the received ultrasonic signal arises from at least one stepped reflector which returns multiple ultrasonic signal reflections.

7. The method of claim 1, wherein the received ultrasonic signal arises from at least one movable reflector.

8. The method of claim 1, wherein the blood is diluted to achieve a monotonic correlation between backscatter and at least one of the properties.

9. A method for measuring one or more of HCT, HGB, MCV, RBC, MCHC, MCH, or TPC of blood, comprising:
collecting a sample of blood of 1 mL or less in a spatially defined capillary tube of a disposable sampling device wherein said sample of blood is retained;
placing said disposable sampling device in a testing region inside said disposable sampling device;
sending one or more ultrasonic signals into the blood sample while still retained in the disposable sampling device;
receiving at least one ultrasonic signal from the blood sample;
measuring at least one characteristic of said ultrasonic signals in said blood sample, said characteristic being selected from the group consisting of time of flight, amplitude and backscatter energy,
calculating from said at least one measured characteristic at least one property of said blood sample, said property being selected from the group consisting of the attenuation coefficient, backscatter coefficient, speed of sound through the sample, and combinations thereof; and
determining at least one property of said blood sample from said calculated property of said returned ultrasonic signals, said property of said blood sample being selected from the group consisting of HCT, HGB, MCV, RBC, MCHC, MCH, TPC, and combinations thereof, of the blood.

10. The method of claim 9, wherein the received ultrasonic signal comprises at least one selected from the group consisting of signals received from two or more acoustic paths, signals received from more than one reflective interface, and a combination thereof.

11. The method of claim 10, wherein said signals are used in combination to eliminate one or more delays or transit times through one or more other materials from the calculation of transit time through blood.

12. The method of claim 9, wherein the measuring comprises measuring a combination of least two of the characteristics to eliminate at least one unknown variable selected from the group consisting of a distance traveled by said one or more ultrasonic signals sent into said blood sample, a temperature of said blood sample, and a combination thereof.

13. The method of claim 9, wherein one or more ultrasonic signal reflections are measured.

14. The method of claim 9, wherein the received ultrasonic signal arises from at least one stepped reflector which returns multiple ultrasonic signal reflections.

15. The method of claim 9, wherein the received ultrasonic signal arises from at least one movable reflector.

16. The method of claim 9, wherein the blood is diluted to achieve a monotonic correlation between backscatter and at least one of the properties.

17. A method for measuring one or more of HCT, HGB, MCV, RBC, MCHC, MCH, or TPC of blood, comprising:
Collecting and containing a blood sample of 1 mL or less in a spatially defined sampling device;
introducing said sampling device into an analyzer;
sending one or more ultrasonic signals from said analyzer into said blood sample while resident in said sampling device;
measuring a characteristic of more than one received ultrasonic signals, said characteristic being any one from among the group consisting of time of flight, amplitude, backscatter energy, and combinations thereof;
calculating a characteristic of said more than one received ultrasonic signals in said blood sample, said calculated characteristic being any one from among the group consisting of speed of sound, attenuation coefficient and backscatter coefficient; and
determining from said calculated characteristic property of said more than one received ultrasonic signals at least one property of said blood sample selected from the group consisting of HCT, HGB, MCV, RBC, MCHC, MCH, TPC, and combinations thereof, of the blood.

18. The method of claim 17, wherein the received ultrasonic signals comprise at least one selected from the group consisting of signals received from two or more acoustic paths, signals received from more than one reflective interface, and a combination thereof.

19. The method of claim 17, wherein said signals are used in combination to eliminate one or more delays or transit times through one or more other materials from the calculation of transit time through blood.

20. The method of claim 17, wherein the measuring comprises measuring a combination of least two characteristics selected from the group consisting of speed of sound, attenuation, temperature, and backscatter to eliminate at least one unknown variable selected from the group consisting of a distance traveled by said one or more ultrasonic signals sent into said blood sample, a temperature of said blood sample, and a combination thereof.

21. The method of claim 17, wherein the received ultrasonic signals arise from at least one stepped reflector which returns multiple ultrasonic signal reflections.

22. The method of claim 17, wherein the received ultrasonic signals arise from at least one movable reflector.

23. The method of claim 17, wherein the blood is diluted to achieve a monotonic correlation between backscatter and at least one of the properties.

24. The method of claim 17, wherein the blood sample is comprised within the body of a subject.

25. A method for measuring one or more of HCT, HGB, MCV, RBC, MCHC, MCH, or TPC of blood, comprising:

collecting and containing in a spatially defined container a blood sample of 1 mL or less;

sending one or more ultrasonic signals into said blood sample;

measuring a characteristic of one or more received ultrasonic signals, said characteristic being any one from among the group consisting of time of flight, amplitude, backscatter energy, and combinations thereof;

measuring a temperature of said blood sample;

calculating a combination of more than one characteristic of said one or more received ultrasonic signals, said combination of characteristics being selected from the group consisting of attenuation coefficient, backscatter coefficient, and speed of sound; and using a combination of said measured temperature and said combination of calculated characteristics of said one or more received ultrasonic signals to determine at least one property of said blood sample selected from the group consisting of HCT, HGB, MCV, RBC, MCHC, MCH, TPC, and combinations thereof.

26. The method of claim 25, wherein the received ultrasonic signal comprises at least one selected from the group consisting of signals received from two or more acoustic paths, signals received from more than one reflective interface, and a combination thereof.

27. The method of claim 26, wherein said signals are used in combination to eliminate one or more delays or transit times through one or more other materials from the calculation of the one or more ultrasonic signals' transit time through blood.

28. The method of claim 25, further comprising measuring a combination of least two characteristics of said at least one received ultrasonic signal selected from the group consisting of time of flight, amplitude, and backscatter energy, to eliminate at least one unknown variable selected from the group consisting of a distance traveled by said one or more ultrasonic signals sent into said blood sample, a temperature of said blood sample, and a combination thereof.

29. The method of claim 25, wherein one or more ultrasonic signal reflections are measured.

30. The method of claim 25, wherein the received ultrasonic signal arises from at least one stepped reflector which returns multiple ultrasonic signal reflections.

31. The method of claim 25, wherein the received ultrasonic signal arises from at least one movable reflector.

32. The method of claim 25, wherein the blood is diluted to achieve a monotonic correlation between backscatter and at least one of the properties.

33. A method for measuring one or more of HCT, HGB, MCV, RBC, MCHC, or MCH of blood, comprising:

collecting a blood sample of 1 mL or less in a spatially defined capillary tube;

introducing said capillary tube into an analyzer;

moving said blood sample from said capillary tube into a testing region;

sending one or more ultrasonic signals into said blood sample while in said testing region;

measuring more than one parameter of at least one ultrasonic signal received from the blood sample selected from the group consisting of time of flight, amplitude and backscatter energy and combinations thereof;

determining from said parameters a characteristic of said at least one received ultrasonic signals selected from the group consisting of speed of sound, attenuation coefficient and backscatter coefficient;

determining at least one property of said blood sample selected from the group consisting of HCT, HGB, MCV, RBC, MCHC MCH, and combinations thereof, of the blood;

wherein the one or more ultrasound signals traverse said testing region through the blood sample.

34. The method of claim 33, wherein the received ultrasonic signal comprises at least one selected from the group consisting of signals received from two or more acoustic paths, signals received from more than one reflective interface, and a combination thereof.

35. The method of claim 33, wherein said signals are used in combination to eliminate one or more delays or transit times through one or more other materials from the calculation of transit time through blood.

36. The method of claim 33, wherein the measuring step further comprises measuring the temperature of the blood sample.

37. The method of claim 36, wherein the measuring step comprises measuring a combination of at least two of the characteristics selected from the group comprising temperature of the blood sample, time of flight of the ultrasonic signal, amplitude of the ultrasonic signal and backscatter energy of the ultrasonic signal to eliminate at least one unknown variable selected from the group consisting of a distance traveled by said one or more ultrasonic signals sent into said blood sample, a temperature of said blood sample, and a combination thereof.

38. The method of claim 33, wherein one or more ultrasonic signal reflections are measured.

39. The method of claim 33, wherein the received ultrasonic signal arises from at least one stepped reflector which returns multiple ultrasonic signal reflections.

40. The method of claim 33, wherein the received ultrasonic signal arises from at least one movable reflector.

41. The method of claim 33, wherein the blood is diluted to achieve a monotonic correlation between backscatter and at least one of the properties.

* * * * *